US00PP23469P2

(12) United States Plant Patent
Dümmen

(10) Patent No.: US PP23,469 P2
(45) Date of Patent: Mar. 12, 2013

(54) ***SCAEVOLA* PLANT NAMED 'DUESCALBU'**

(50) Latin Name: *Scaevola aemula*
Varietal Denomination: Duescalbu

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 0 days.

(21) Appl. No.: 13/317,901

(22) Filed: Oct. 31, 2011

(51) Int. Cl.
*A01H 5/00* (2006.01)

(52) U.S. Cl. ..... Plt./363

(58) Field of Classification Search ..... Plt./363
See application file for complete search history.

*Primary Examiner* — Kent L Bell
(74) *Attorney, Agent, or Firm* — C. A. Whealy

(57) ABSTRACT

A new and distinct cultivar of *Scaevola* plant named 'Duescalbu', characterized by its semi-compact, mounded and outwardly spreading plant habit; moderately vigorous growth habit; freely branching habit; freely flowering habit; violet-colored flowers; and good container and garden performance.

1 Drawing Sheet

Botanical designation: *Scaevola aemula*.
Cultivar denomination: 'DUESCALBU'.

BACKGROUND OF THE INVENTION

The present invention relates to a new and distinct cultivar of *Scaevola* plant, botanically known as *Scaevola aemula* and hereinafter referred to by the name 'Duescalbu'.

The new *Scaevola* plant a product of a planned breeding program conducted by the Inventor in Rheinberg, Germany. The objective of the breeding program is to create compact and freely branching *Scaevola* plants with numerous attractive flowers.

The new *Scaevola* plant originated from a cross-pollination conducted by the Inventor in Rheinberg, Germany in July, 2007 of a proprietary selection of *Scaevola aemula* identified as code number F-019-001, not patented, as the female, or seed, parent with a proprietary selection of *Scaevola aemula* identified as code number F-02-001, not patented, as the male, or pollen, parent. The new *Scaevola* plant was discovered and selected by the Inventor as a single flowering plant from within the progeny of the stated cross-pollination in a controlled environment in Rheinberg, Germany in May, 2010.

Asexual reproduction of the new *Scaevola* plant by vegetative cuttings in a controlled environment in Rheinberg, Germany since June, 2010 has shown that the unique features of this new *Scaevola* plant are stable and reproduced true to type in successive generations.

SUMMARY OF THE INVENTION

Plants of the new *Scaevola* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Duescalbu'. These characteristics in combination distinguish 'Duescalbu' as a new and distinct *Scaevola* plant:

1. Semi-compact, mounded and outwardly spreading plant habit.
2. Moderately vigorous growth habit.
3. Freely branching habit.
4. Freely flowering habit.
5. Violet-colored flowers.
6. Good container and garden performance.

Plants of the new *Scaevola* can be compared to plants of the parent selections. Plants of the new *Scaevola* differ from plants of the parent selections in the following characteristics:

1. Plants of the new *Scaevola* are more compact than plants of the parent selections.
2. Plants of the new *Scaevola* are more freely branching than plants of the parent selections.

Plants of the new *Scaevola* can be compared to plants of the *Scaevola aemula* 'Wesscaetob', disclosed in U.S. Plant Pat. No. 19,658. In side-by-side comparisons, plants of the new *Scaevola* differed from plants of the 'Wesscaetob' in the following characteristics:

1. Plants of the new *Scaevola* were more vigorous than plants of 'Wesscaetob'.
2. Plants of the new *Scaevola* had longer internodes than plants of 'Wesscaetob'.
3. Plants of the new *Scaevola* and 'Wesscaetob' differed slightly in flower color.

BRIEF DESCRIPTION OF THE PHOTOGRAPH

The accompanying colored photograph illustrates the overall appearance of the new *Scaevola* plant showing the colors as true as it is reasonably possible to obtain in colored reproductions of this type. Colors in the photograph may differ slightly from the color values cited in the detailed botanical description which accurately describe the colors of the new *Scaevola* plant.

The photograph comprises a side perspective view of a typical flowering plant of 'Duescalbu' grown in a container.

DETAILED BOTANICAL DESCRIPTION

The aforementioned photograph and following observations, measurements and values describe plants grown during the summer in 12-cm containers in a glass-covered greenhouse in Rheinberg, Germany and under environmental conditions and cultural practices which closely approximate commercial *Scaevola* production. During the production of the plants, day and night temperatures averaged 18° C. and light levels averaged 4,500 lux. Plants were pinched three weeks after planting and were 20 weeks old when the photograph and detailed description were taken. In the following description, color references are made to The Royal Horticultural Society Colour Chart, 1995 Edition, except where general terms of ordinary dictionary significance are used.

Botanical classification: *Scaevola aemula* 'Duescalbu'.

Parentage:

*Female, or seed, parent*.—Proprietary selection of *Scaevola aemula* identified as code number F-019-001, not patented.

*Male or pollen parent*.—Proprietary selection of *Scaevola aemula* identified as code number F-02-001, not patented.

Propagation:

*Type*.—By vegetative cuttings.

*Time to initiate roots, summer*.—About five days at about 20° C.

*Time to initiate roots, winter*.—About ten days at about 20° C.

*Time to develop roots, summer*.—About three weeks at about 20° C.

*Time to develop roots, winter*.—About four weeks at about 20° C.

*Root description*.—Fine, fibrous; white in color.

*Rooting habit*.—Freely branching; dense.

Plant description:

*Plant form and growth habit*.—Semi-compact, mounded and spreading plant habit; moderately vigorous growth habit.

*Branching habit*.—Freely branching, lateral branches potentially forming at every node; pinching enhances branching potential.

*Plant height*.—About 8 cm.

*Plant diameter* (*area of spread*).—About 12 cm.

Lateral branch description:

*Length*.—About 10 cm.

*Diameter*.—About 3 mm.

*Internode length*.—About 3.3 cm.

*Aspect*.—Outwardly spreading.

*Texture*.—Smooth, glabrous.

*Color*.—Close to 148A and 145A to 145B.

Foliage description:

*Arrangement*.—Alternate, simple.

*Length*.—About 5.2 cm.

*Width*.—About 1.9 cm.

*Shape*.—Oblanceolate.

*Apex*.—Acute.

*Base*.—Attenuate.

*Margin*.—Serrate.

*Texture, upper and lower surfaces*.—Smooth, glabrous.

*Venation pattern*.—Pinnate.

*Color*.—Developing leaves, upper surface: Close to 147A. Developing leaves, lower surface: Close to 146A. Fully expanded leaves, upper surface: Close to 147A; venation, close to 147A. Fully expanded leaves, lower surface: Close to 146B; venation, close to 146B.

*Petiole length*.—About 9 mm.

*Petiole diameter*.—About 2 mm.

*Petiole texture, upper and lower surfaces*.—Smooth, glabrous.

*Petiole color, upper and lower surfaces*.—Close to 145A.

Flower description:

*Flower type and shape*.—Zygomorphic, semi-circular, fan-shaped flowers with five petals fused at the base to form a tubular flower throat; flower throat open along the upper surface exposing reproductive organs.

*Flower arrangement and quantity*.—Solitary sessile flowers arising from leaf axils; flowers face upright to outwardly; freely flowering habit with typically about five flowers developing per lateral branch.

*Flowering time*.—Plants begin flowering after about six weeks after planting; in Germany, plants flower continuously during the spring in the garden and outdoor nurseries.

*Flower longevity*.—Flowers typically last about five to seven days on the plant; flowers not persistent.

*Fragrance*.—None detected.

*Flower buds*.—Shape: Ensiform. Length: About 1.2 cm. Diameter: About 2 mm. Color: Close to 145C and 84A.

*Flowers*.—Diameter: About 1.5 cm. Height: About 8 cm.

*Petals*.—Quantity: Five, fused at base. Shape: Elliptic. Apex: Acute. Margin: Entire. Length: About 2.5 cm. Width: About 1.5 mm. Texture, upper and lower surfaces: Smooth, glabrous. Color: When opening, upper surface: Close to 88A. When opening, lower surface: Close to 88C. Fully opened, upper surface: Close to 88B; color becoming closer to 88C with development. Fully opened, lower surface: Close to 88C; color becoming closer to 88D with development.

*Sepals*.—Quantity: Two per flower. Length: About 5 mm. Width: About 1 mm. Shape: Lanceolate. Apex: Acute. Base: Obtuse. Margin: Entire. Texture, upper and lower surfaces: Slightly pubescent. Color, upper and lower surfaces: Close to 137A.

*Reproductive organs*.—Androecium: Stamen quantity per flower: About five. Filament length: About 4.5 mm. Filament color: Close to 163C. Anther shape: Rounded. Anther length: About 1 mm. Anther color: Close to 177A. Pollen: Scarce. Pollen color: Close to 3B. Gynoecium: Pistil quantity per flower: One. Pistil length: About 1.2 cm. Style length: Close to 8.5 mm. Style color: Close to 59A. Stigma shape: V-shaped. Stigma color: Close to 144C and 155A. Ovary color: Close to 144A.

*Seeds and fruits*.—Seed and fruit development have not been observed on plants of the new *Scaevola*.

Garden performance: Plants of the new *Scaevola* have been observed to have good garden performance and to tolerate rain, wind and temperatures ranging from about 5° C. to about 40° C.

Pathogen/pest resistance: Plants of the new *Scaevola* have not been shown to be resistant to pathogens and pests common to *Scaevola*.

It is claimed:

1. A new and distinct *Scaevola* plant named 'Duescalbu' as illustrated and described.

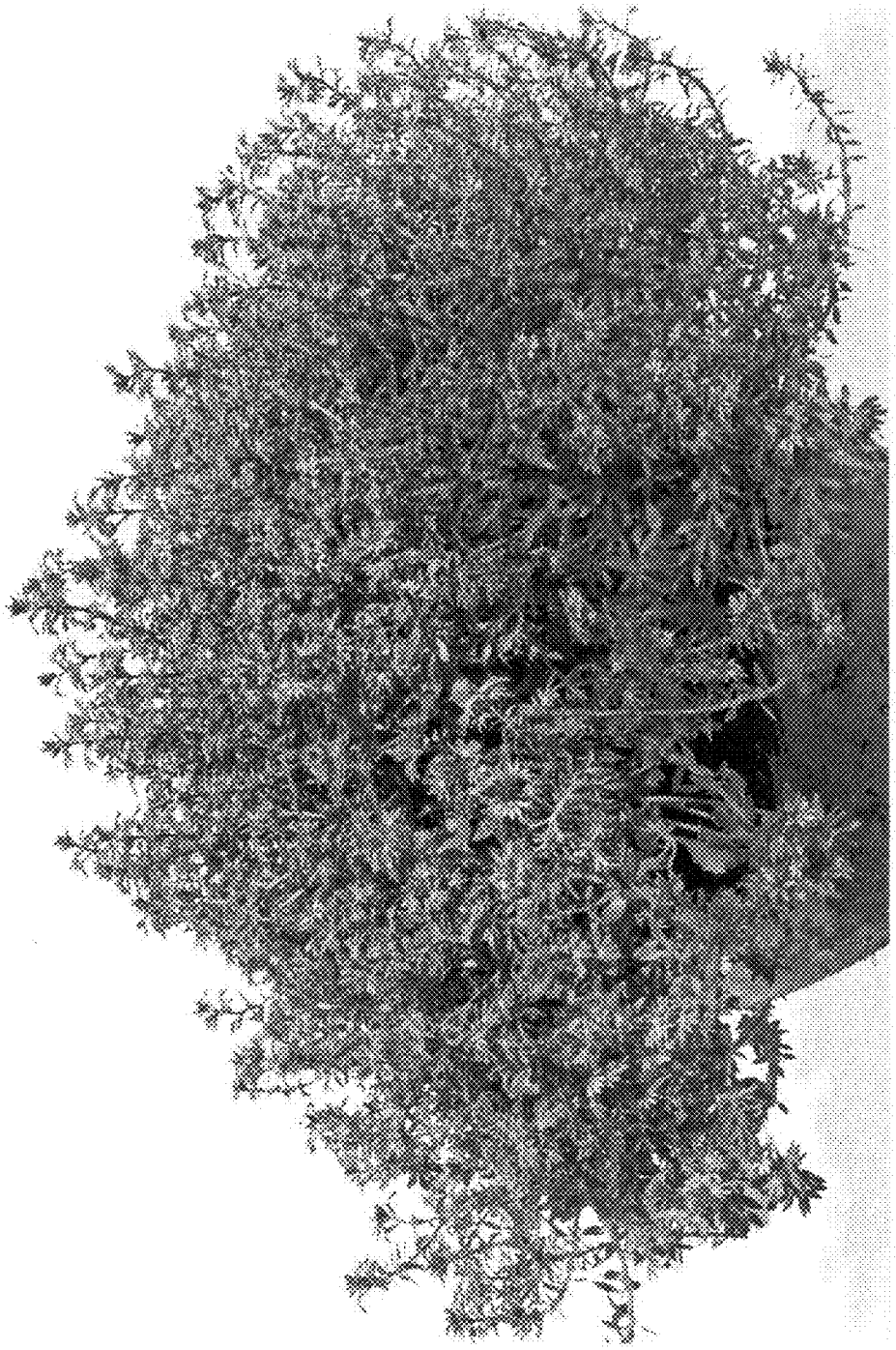

* * * * *